(12) United States Patent
Slater

(10) Patent No.: US 7,993,590 B2
(45) Date of Patent: Aug. 9, 2011

(54) AIR FRESHENING SYSTEM

(76) Inventor: Roderick Slater, Silver Spring, MD (US)

( * ) Notice: Subject to any disclaimer, the term of this patent is extended or adjusted under 35 U.S.C. 154(b) by 109 days.

(21) Appl. No.: 12/105,903

(22) Filed: Apr. 18, 2008

(65) Prior Publication Data

US 2008/0260595 A1  Oct. 23, 2008

Related U.S. Application Data

(60) Provisional application No. 60/912,628, filed on Apr. 18, 2007.

(51) Int. Cl.
*A61L 9/04* (2006.01)

(52) U.S. Cl. ............ 422/123; 422/120; 239/34; 239/53; 239/56; 239/57

(58) Field of Classification Search ............... D23/366; 239/34, 53, 56, 57; 422/120, 123
See application file for complete search history.

(56) References Cited

U.S. PATENT DOCUMENTS

| | | | | |
|---|---|---|---|---|
| 5,547,636 | A * | 8/1996 | Vick et al. | 422/124 |
| 5,695,692 | A * | 12/1997 | Kennedy | 261/30 |
| 6,764,656 | B1 * | 7/2004 | Matulevich | 422/124 |
| 2006/0118976 | A1* | 6/2006 | Hoffman | 261/24 |
| 2006/0251541 | A1* | 11/2006 | Santandrea | 422/5 |
| 2008/0099576 | A1* | 5/2008 | Hart | 239/53 |

* cited by examiner

*Primary Examiner* — Sean E Conley

(57) ABSTRACT

A sports team display system combined with vehicle air freshener that aids in a vehicle driver's ability to prominently display his or her support for an athletic team or organization while at the same time provides a pleasant smell to emit throughout the interior of the vehicle. The system is designed so that it will remain in a stationary position while continuing to prominently display itself while emitting the pleasant smell.

10 Claims, 8 Drawing Sheets

AIR FRESHENING SYSTEM

This is a non-provisional application claiming priority to provisional patent application No. 60/912,628 filed on Apr. 18, 2007.

FIELD OF THE INVENTION

The present invention relates to the placement of a circular base, affixing the circular base with a ridged air freshener disc holder, confining an air freshener disc to the air freshener disc holder, and inserting a rod that ultimately permits a user to prominently display a miniature athletic sporting symbol or piece of equipment at the rear of a vehicle or other relatively flat surface while at the same time allowing for a pleasant-smelling interior. In addition, the user also can place the air freshener disc in a position that emulates real sporting activity such as servicing an actual racecar.

BACKGROUND OF THE INVENTION

Like many people, there is no question that sports fans spend significant amounts of time in their vehicles. While driving, sports fans often like to express their support for a particular professional, college, and even high-school athletic team. Bumper stickers, flags and even state-sanctioned license plates all serve to proclaim a vehicle owner's support for a particular team. It is not uncommon to see a flag mounted on a vehicle as it flutters in the wind while displaying the logo of a professional or college athletic team. It does not matter if it is football, baseball, basketball, hockey or some other sport. People support their teams and like to express that support on their vehicles. This should be no surprise because vehicles are out in public and can be seen by virtually everybody within the vicinity. And again, since sports fans spend as much time as anyone else driving, it must come as no surprise that they often choose their vehicles as the conduit for which to express their team support.

While items such as bumper stickers and flags support the various teams on the external portions of the vehicle, sports fans also have proven that they enjoy placing team-oriented items inside their vehicles as well. One relevant example is that many people place items such as baseball caps on the shelf area adjacent to the rear window of the vehicle. People also have been known to place stuffed animals and royal crowns in this location. But by placing these team-oriented items at the rear window, virtually anybody moving behind the vehicle will see that the driver is a fan of that particular sports team. Moreover, by placing such an item in the interior of the vehicle, it is much better protected from outside elements.

Meanwhile, sports fans are generally like most other people in that they enjoy a pleasant-smelling vehicle. In fact, air fresheners are very commonly found on the inside of vehicles. Recognizing that sports fans are a part of this market, some people have attempted to cater the interest in sports teams to those desiring a pleasant-smelling vehicle. This has prompted the creation of football helmets doubling as air fresheners. However, these items all have one thing in common. This is the fact that they all are designed to hang from a built-in aspect of the vehicle such as the rear-view mirror.

The current designs in regard to combining sports team support and pleasant smell have some inherent flaws that ultimately serve to defeat the purpose. For a big sports team supporter, an item such as a football helmet dangling and swaying back and forth from the rear-view mirror hardly proclaims that the vehicle is being driven by a big supporter of that particular team. For one thing, most people outside of the vehicle would not notice a football helmet or baseball cap dangling from the rear-view mirror. In traffic, much more people are prone to looking at the back of a vehicle than the front. In addition, people driving behind a vehicle have more time and can easier and safely view items at the rear window as opposed to an item dangling way up in the front of the vehicle. Therefore, there is a need for an air freshener that can properly proclaim and be seen by those outside the vehicle that this particular vehicle is being driven by a fan of the particular sports team.

Another aspect about these current designs is that current dangling air fresheners can be distracting. Unless the vehicle is stopped for a period of time, the basic movements of the vehicle will cause a dangling air freshener, especially those depicting sports teams and equipment, to move and sway. Human eyes are attracted to motion, which means that these dangling air fresheners can be very distracting as they sway and rock back and forth while the vehicle is in operation. In particularly bumpy road conditions, the swaying and rocking of these dangling air fresheners can be even more violent and thus more distracting. Again, there remains a need for an air freshener also serving as a proclamation of a sports fan's support for a particular team that can remain stationary and immobile.

The present invention satisfies this need. By placing the present invention at the rear shelf of a vehicle, the circular base is such that the sports display will not move during bumpy conditions on the road. Placing a rod through the ridged circular holder and air freshener disc also serves to immobilize the present invention while also allowing for such displays of support for NASCAR™ drivers and football teams. Particularly with the racecar sports symbol, the present invention not only allows a user to achieve a pleasant smelling vehicle while prominently display his or her affinity for a particular driver or racecar. But the user also may even emulate such tasks as changing an air filter of a real racecar through the method of changing or replacing the air freshener disc.

SUMMARY OF THE INVENTION

The present invention uses a circular base to support an overall system designed to sit stationary close to the rear window of a vehicle. While using the circular base to maintain an immobile system to contain an air freshener disc holder for an ultimate pleasant smelling vehicle interior, the present invention serves a dual purpose by also possessing the ability to prominently display a sports team symbol. This symbol can be a specially crafted football helmet, baseball cap, basketball, hockey mask or other symbol relating to a preferred sports team. In addition, the air freshener can be placed underneath the hood of an auto-racing vehicle display.

As mentioned above, the circular base is of a proper weight and material so that it will remain stationary while resting on the shelf area or comparable area adjacent to the rear window on the interior of a vehicle. Connected on top of the circular base is the air freshener disc holder. The air freshener disc holder maintains a hole in the middle of its circular dimension. In addition, the air freshener disc holder has elevated sides that permit easy placement of an air freshener disc. The air freshener disc emits a pleasant smell. This air freshener disc also has a hole in the middle of its circular characteristic.

From this point, the present invention features a sports symbol such as a football helmet, baseball or basketball. The sports symbol connects to the circular base via the attached air freshener disc holder through the use of a clip/snap device attached to a rod that effectively locks the sports symbol in place with the air freshener disc holder and circular base. The rod is located and connected in the middle interior of the sports symbol. The rod snugly fits into the holes in the center of the air freshener disc, air freshener disc holder and finally through the air freshener disc holder where the clip/snap device ultimately interlocks the rod to the rest of the present invention.

The rod's connection between the sports symbol and air freshener disc holder in the middle of the present invention helps keep the present invention balanced and stationary to accommodate the movement of the vehicle while the present invention is positioned adjacent to the rear window. In this way, the present invention does not sway or move in any way, as it is firmly stationary and positioned in the best possible and safest location for public display of support for the particular sports team or organization.

The preferred embodiment of the present invention is to use a miniature replica of a professional, college or high-school football helmet as the sports symbol. In this instance, the pleasant smell from the air freshener can freely flow away from the air freshener disc and into the interior of the vehicle. However, virtually any sports symbol can apply to the present invention. Miniature replica baseball caps, baseballs, basketballs and hockey masks also are examples of sports symbols that can be crafted via holes, openings and other elements to permit the free flow of the pleasant smell while also proclaiming support for a sports team.

DETAILED DESCRIPTION OF THE PREFERRED EMBODIMENT

Figure 1:
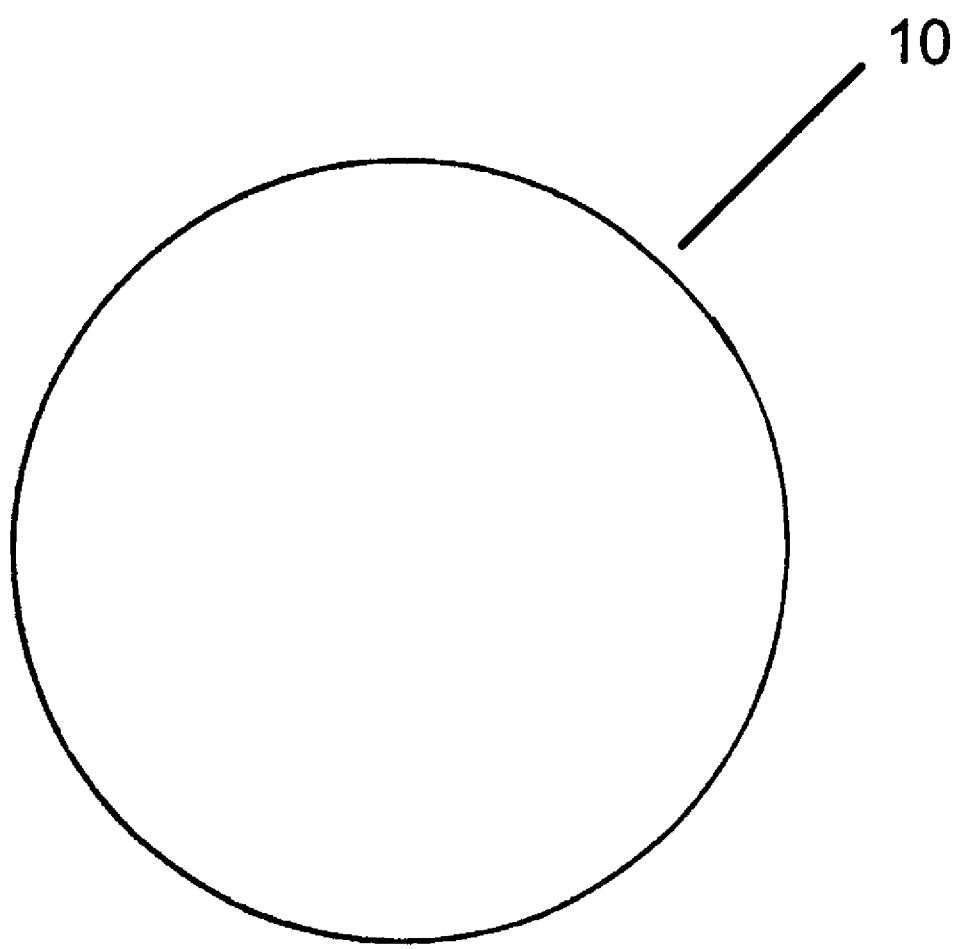
FIG. 1 is a top view of the circular base (10) of the present invention
Figure 2:
FIG. 2 is a side view of the circular base (10) of the present invention

FIG. 1 shows us a view of the circular base (10) of the present invention. The circular base (10) is made of a sturdy and relatively rough material such as rubber. Material such as rubber is advantageous because it provides enough weight to maintain the present invention's immobile and stationary condition without swaying or tipping. As seen in FIG. 2, the circular base (10) is the grounding foundation of the present invention that utilizes its relatively rough material and sturdy weight to prevent the present invention from sliding or tipping as it rests in the back of the vehicle near the rear window. The circular base is affixed to the air freshener disc holder (20) of FIG. 3 and FIG. 4.

Figure 3:
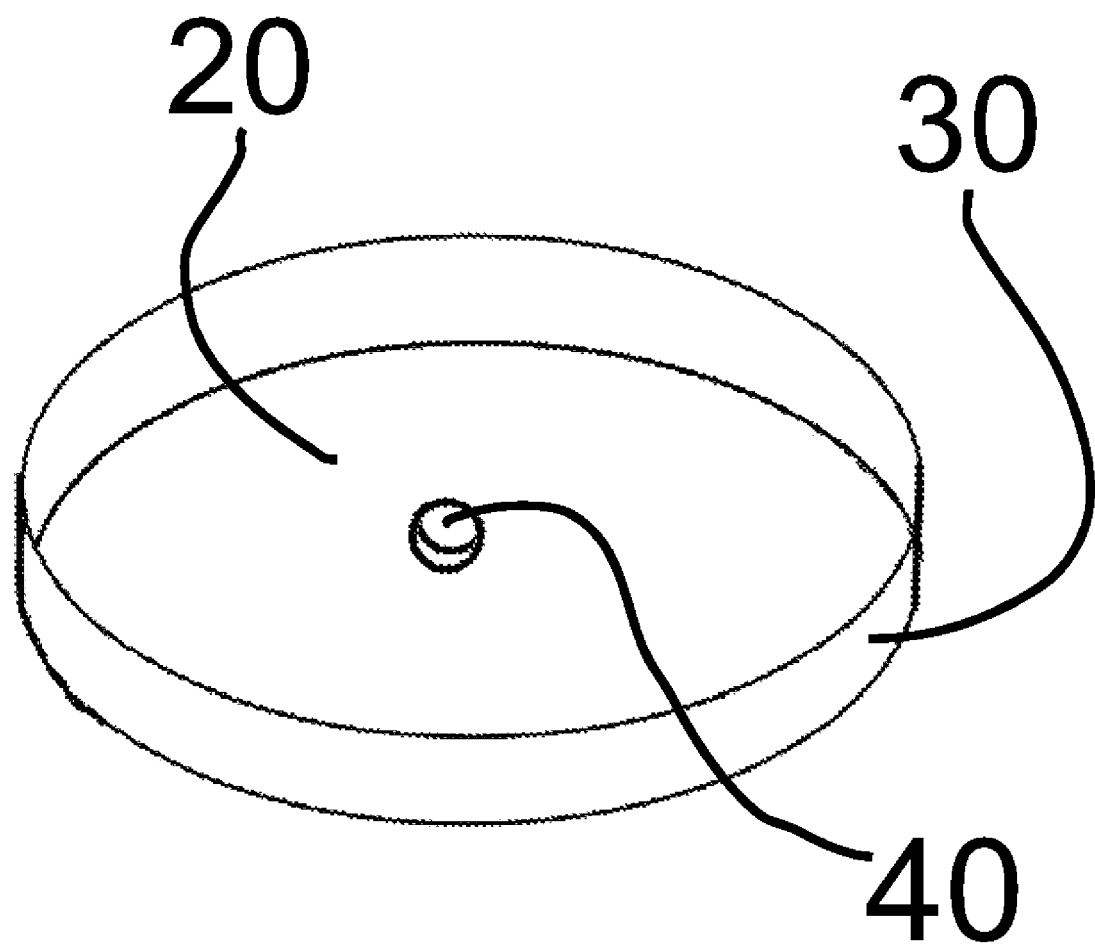
FIG. 3 is a side view of the air freshener disc holder (20) of the present invention
Figure 4:
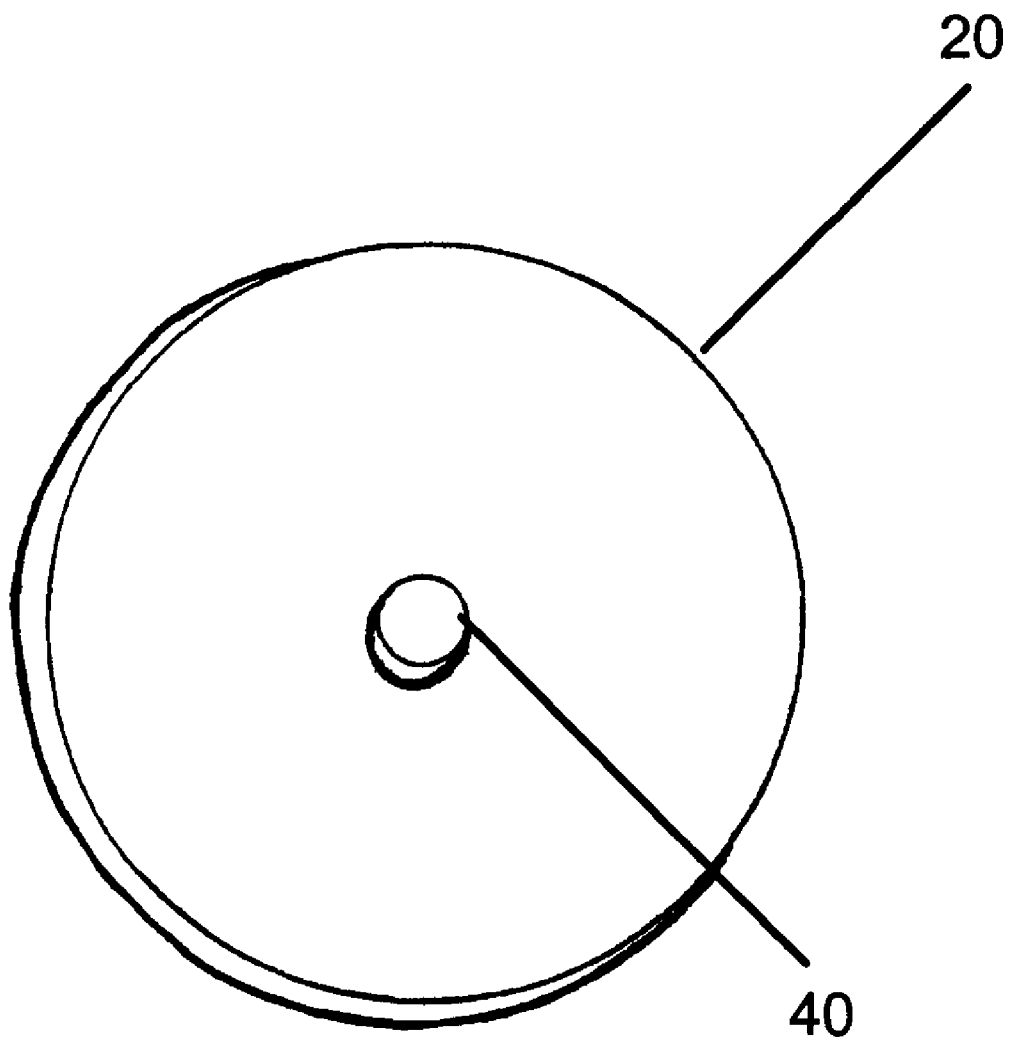
FIG. 4 is a top view of the air freshener disc holder (20) of the present invention

As an element that is affixed to the circular base (10), the air freshener disc holder (20) is roughly the same diameter as the circular base (10). The air freshener disc holder (20) of FIG. 3 and FIG. 4 is comparable to a dish in that it is meant to have the air freshener disc (45) placed within its confines. Elevated ridges (30) protrude from the sides of the air freshener disc holder (20) to better house the air freshener disc (45) in regard to its height. In FIG. 4, we see that the air freshener disc holder (20) has an air freshener disc holder hole (40) located in the middle of the air freshener disc holder (20). In a preferred embodiment of the present invention, the air freshener disc holder hole (40) begins relatively thinner at the top of the air freshener disc holder hole (40) and then slightly widens its diameter as the rod (50) is placed deeper. The reason for this widening aspect is because the rod (50) of FIG. 6 contains a lower clip/snap device (60) that somewhat resembles a downward-pointing, slightly flexible arrow. When the lower clip/snap device (60) of the rod (50) reaches the top of the air freshener disc holder hole (40), the thin nature of the top will cause the lower clip/snap device (60) to slightly bend. However, once the lower clip/snap device (60) is pushed through the thinner top portion of the air freshener disc holder hole (40), the confines will widen enough so that the lower clip/snap device (60) will cease bending and will snap into its natural position inside the air freshener disc holder (20).

Figure 5:
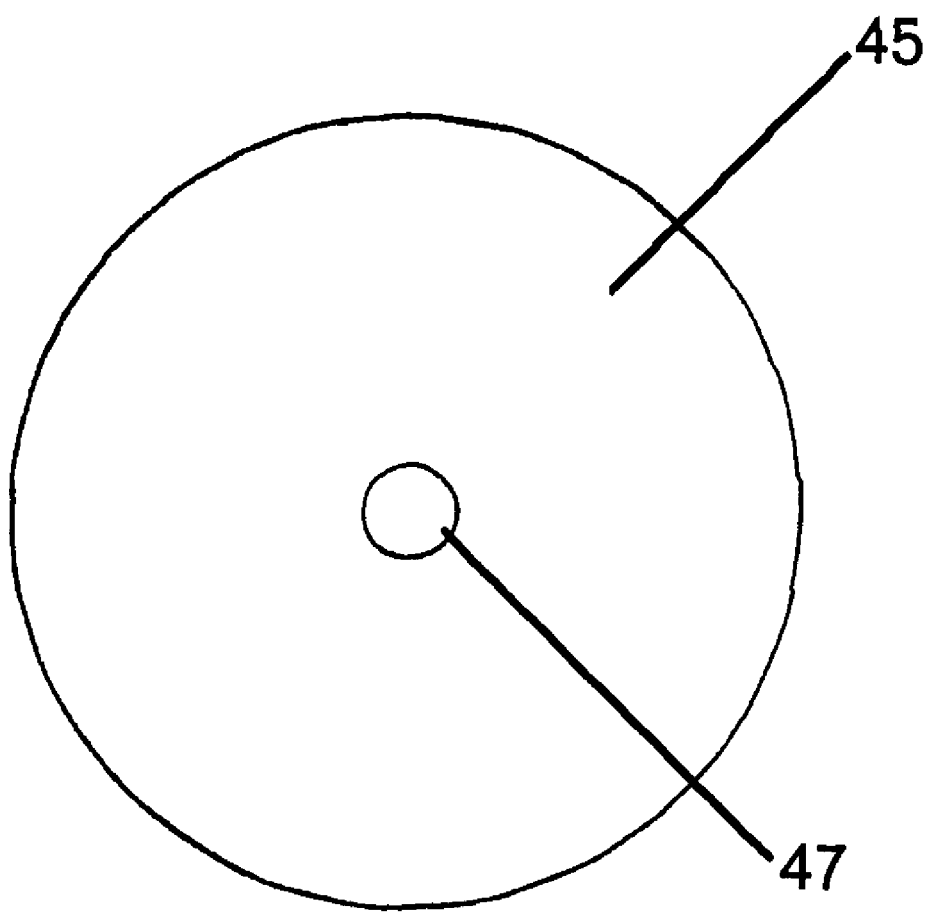
FIG. 5 is a top view of an air freshener disc (45) of the present invention

However, before the rod (50) is placed through the center of the present invention, the air freshener disc (45) is rested into the air freshener disc holder (20). The air freshener disc (45) as seen in FIG. 5 is just smaller in diameter than the air freshener disc holder (20) so that it fits snuggly inside. The air freshener disc (45) is of the sort that permeates a pleasant smell through contact with air. The air freshener disc (45) also has an air freshener disc hole (47) in the middle that is placed directly above the air freshener disc holder hole (40). This air freshener disc hole (47) is of the same width as the top portion of the air freshener disc holder hole (40). Because of this width factor, the lower clip/snap device (60) will slightly bend as it reaches the air freshener disc hole (47) and will stay slightly bent until it reaches the wider portion of the air freshener disc holder hole (40).

Figure 6:
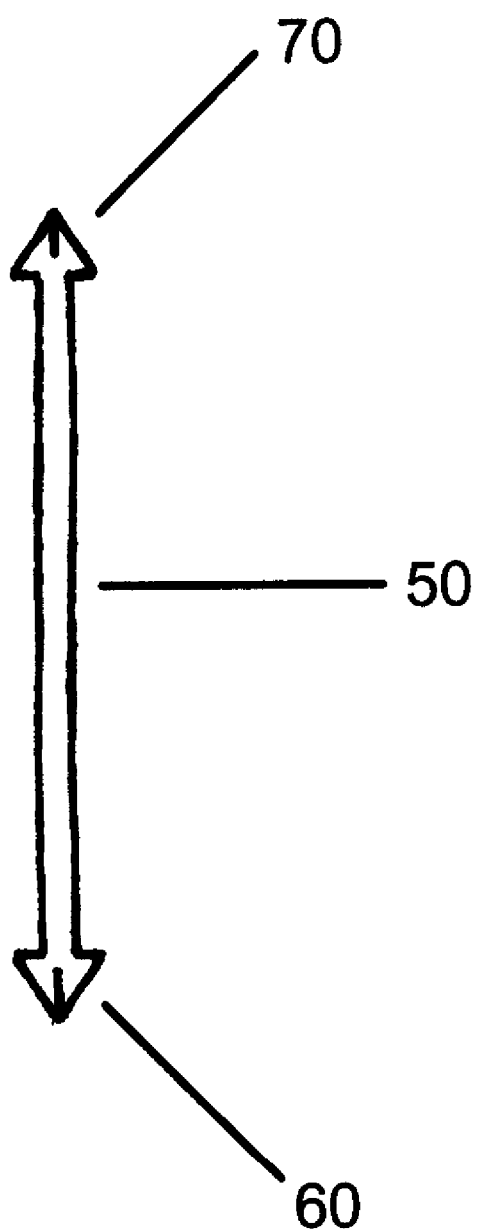
FIG. 6 is a side view of the rod (50) of the present invention

FIG. 6 shows us the makeup of the overall rod (50) of the present invention. The rod (50) is a sturdy shaft that contains two elements, one at the top and one at the bottom. These elements as seen in FIG. 6 are the lower clip/snap device (60) and the upper clip/snap device (70). As described above, the lower clip/snap device (60) bends slightly as it is placed through the air freshener disc hole (47), which is relatively thin, and the top of the air freshener disc holder hole (40). As described above, as the air freshener disc holder hole (40) widens as the lower clip/snap device (60) moves deeper, the lower clip/snap device (60) will then snap back into its natural position as enough room becomes available. This aspect of the present invention allows for the rod (50) to be attached to the air freshener disc (45), air freshener disc holder (20) and by natural affixation, the circular base (10).

Figure 7:
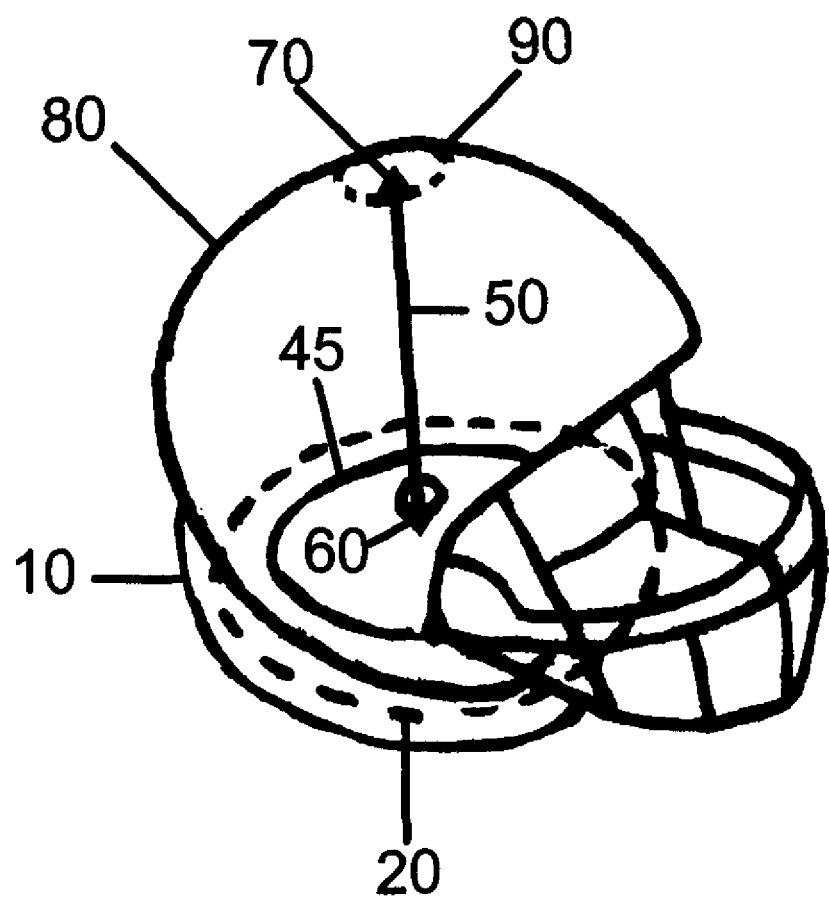
FIG. 7 is a side view of an embodiment of the present invention

Another primary aspect of the rod (50) is that it is the sturdy connection between the sports symbol (80) and the rest of the present invention. In FIG. 7, we see a view of the entire present invention. In FIG. 7, an embodiment of the sports symbol (80) is a miniature football helmet. However, it should be noted that this is merely an example of a sports symbol (80) as other items such as basketballs, baseballs, baseball caps, hockey masks, hockey pucks, etc can be used with the present invention. Regardless of what the sports symbol (80) actually represents, the interior aspects remain consistent. As we see in FIG. 7, a tube (90) is located in the middle of the sports symbol (80). The tube (90) is sturdy and protrudes out of the interior of the sports symbol (80) where it is connected at the middle. The tube (90) extends downward where there is an opening for the upper clip/snap device (70) of the rod (50). The opening of the tube (90) is relatively thinner and widens out, as the upper clip/snap device (70) is placed upward and ultimately closer to the top of the sports symbol (80). Like the function of its lower clip/snap device (60) counterpart, the upper clip/snap device (70) slightly bends as it first enters the opening of the tube (90). As the tube (90) widens, the upper clip/snap device (70) will finally snap into its natural position. This function connects the sports symbol (80) to the air freshener disc (45), air freshener disc holder (20) and the circular base (10) through the sturdy connection of the rod (50).

As we see in FIG. 7, the sports symbol (80) is wide enough where it covers the elements of the present invention affixed to the circular base (10), as well as the air freshener disc (45). In the preferred embodiment of the present invention, the sports symbol covers most everything, although it does not have to. The rod (50) is the conduit that tightly steadies the present invention to accommodate for the height and width of the sports symbol (80). The attachment of the rod (50) to the tube (90) of the sports symbol (80) and the air freshener disc holder (20) via the upper clip/snap device (70) and lower clip/snap device (60) respectively, causes the present invention to be a singular, integrated system. The circular base (10), meanwhile, adds the additional element of preventing the present invention from sliding or tipping due to its nature and composition.

In this manner, the present invention may rest without movement after being placed on the back shelf of many vehicles, although the circular base (10) can be placed on virtually any surface. In respect to the back shelf of a vehicle, this is a location where people often place items such as stuffed animals, royal crowns and baseball caps in an effort to express support for an idea or athletic team. In respect for sports fans, the present invention provides a sturdy and safe system to express the support for a particular sports team in front of the rear window of a vehicle interior where it can be seen be people on the outside. In addition, the air freshener disc (45) of the present invention provides the dual function of emitting a pleasant smell throughout the vehicle as the odor drifts off of the air freshener disc (45) and through the sports symbol into the interior of the vehicle. The size of the present invention can vary, although the preferred embodiment would confine the present invention to serve in conjunction and compatibility with a 3" tall and 3/16" wide rod (50) along with a 3" circumference for the circular base. This is mainly for safety reasons due to the location of the present invention at the rear window of a vehicle.

The present invention is a display system. The user may place a circular base (10) on a back shelf of a vehicle. However, it should be noted that the back shelf of the vehicle is merely the preferred embodiment. In that regard, the user also may place the circular base (10) on any relatively flat surface such as a desk, shelf, table, etc. An air freshener disc holder (20) is affixed to the circular base (10). The air freshener disc (45) is confined within the air freshener disc holder (20) via elevated ridges (30) protruding from the air freshener disc holder (20) as described above. A lower clip/snap device (60) of a rod (50) is inserted through the air freshener hole. The air freshener hole is located at the center of the air freshener disc (45). The lower clip/snap device (60) of the rod (50) is secured within the air freshener disc holder hole (40). The air freshener disc holder hole (40) is located at the center of the air freshener disc holder (20). The upper clip/snap device (70) of the rod (50) is inserted into a tube (90), the tube (90) being in communication with the sports symbol (80) as described above. The circular base (10) then may be covered with the sports symbol (80). The user may then display the sports symbol (80). The system of the present invention will emit a pleasant smell via the air freshener disc (45).

The air freshener disc holder (20) is formed to have a diameter equal to the diameter of the circular base (10). The sports symbol (80) is hollowed out. Air can then pass through the sports symbol (80) and across the air freshener disc (45). In other words, the air is passed through the sports symbol (80) that has been hollowed out, and passing the air across the air freshener disc (45). The sports symbol (80) also may be opened.

Figure 8:
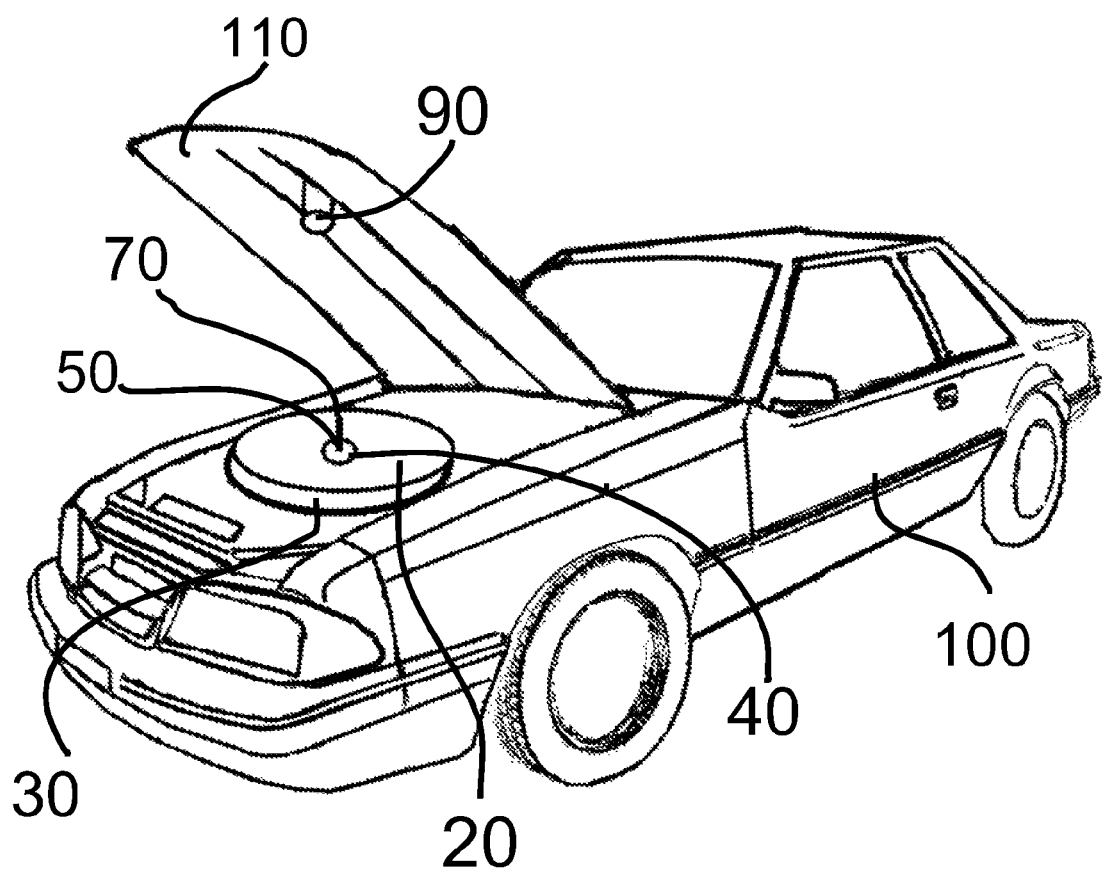
FIG. 8 is a view of a replica racecar embodiment of the present invention.

An additional embodiment of the present invention as seen in FIG. 8 relates to a racecar replica (100). In this embodiment the user places the circular base (10) on a back shelf of a vehicle as described above. Again, the placement on the back shelf of a vehicle is the preferred embodiment, but the user also may place the circular base (10) on a surface that is relatively flat such as a table, desk, shelf, etc. The air freshener disc holder (20) is affixed to the circular base (10). The user then may position the air freshener disc holder (20) into a hood (110) of the racecar replica (100). The user then can open the hood (110) of the racecar replica (100) to emulate servicing an actual racecar. For example, the user can change the air freshener disc (45) to a different smelling or newer air freshener disc (45) while emulating changing or replacing an air filter located inside the hood (110) of a real racecar. The hood (110) is opened and closed via conventional means. In this manner, the user may place the air freshener disc (45) into the hood (110) of the racecar replica (100). The air freshener disc (45) within the air freshener disc holder (20) is confined via the elevated ridges (30) protruding from the air freshener disc holder (20). The user then inserts a lower clip/snap device (60) of a rod (50) through an air freshener hole, the air freshener hole located at the center of the air freshener disc (45). The user then secures the lower clip/snap device (60) of the rod (50) within an air freshener disc holder hole (40), the air freshener disc holder hole (40) located at the center of the air freshener disc holder. The user then can close the hood (110) of the racecar replica (100) by inserting an upper clip/snap device (70) of the rod (50) into a tube (90), the tube (90) being in communication with the hood (110) of the racecar replica (100). The circular base (10) is covered with the racecar replica (100) and the racecar replica (100) is displayed. The system of the present invention in this embodiment also will emit a pleasant smell via the air freshener disc (45). As we see in FIG. 8, the user may open the hood (110) of the racecar replica (100) and place or remove the air freshener disc (45) onto the confines of the air freshener disc holder as seen in FIG. 8. The user then may simply close the hood (110), the tube (90) on the hood (110) connecting with the rod (50) as described above.

I claim:

1. A method of making a display, comprising:
   placing a circular base on a surface;
   affixing an air freshener disc holder to the circular base;
   confining an air freshener disc within the air freshener disc holder via elevated ridges protruding from the air freshener disc holder;
   inserting a lower clip/snap device of a rod through an air freshener hole, the air freshener hole located at the center of the air freshener disc;
   securing the lower clip/snap device of the rod within an air freshener disc holder hole, the air freshener disc holder hole located at the center of the air freshener disc holder;
   inserting an upper clip/snap device of the rod into a tube, the tube being in communication with a sports symbol;
   covering the circular base with the sports symbol;
   displaying the sports symbol; and
   emitting a pleasant smell via the air freshener disc.

2. The method of making a display of claim 1, further comprising forming the air freshener disc holder to have a diameter equal to the diameter of the circular base.

3. The method of making a display of claim 1, further comprising hollowing out the sports symbol.

4. The method of making a display of claim 1, further comprising passing air through the sports symbol and across the air freshener disc.

5. The method of making a display of claim 3, further comprising passing air through the sports symbol and across the air freshener disc.

6. The method of making a display of claim 5, further comprising passing the air through the sports symbol that has been hollowed out, and passing the air across the air freshener disc.

7. The method of making a display of claim 1, further comprising opening the sports symbol.

8. The method of making a display of claim 7, further comprising passing air through the sports symbol and across the air freshener disc.

9. The method of making a display of claim 7, further comprising passing air through the sports symbol and across the air freshener disc.

10. The method of making a display of claim 9, further comprising passing the air through the sports symbol that has been hollowed out, and passing the air across the air freshener disc.

* * * * *